(12) United States Patent
Kuno et al.

(10) Patent No.: US 10,190,088 B2
(45) Date of Patent: Jan. 29, 2019

(54) ORGANISM CULTURING SYSTEM AND ORGANISM CULTURING METHOD

(71) Applicant: Hitachi, Ltd., Chiyoda-ku, Tokyo (JP)

(72) Inventors: Norihito Kuno, Tokyo (JP); Hiroko Tada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 242 days.

(21) Appl. No.: 14/767,448

(22) PCT Filed: Feb. 27, 2013

(86) PCT No.: PCT/JP2013/055032
§ 371 (c)(1),
(2) Date: Aug. 12, 2015

(87) PCT Pub. No.: WO2014/132348
PCT Pub. Date: Sep. 4, 2014

(65) Prior Publication Data
US 2016/0010050 A1    Jan. 14, 2016

(51) Int. Cl.
*C12M 3/00* (2006.01)
*C12M 1/00* (2006.01)
(Continued)

(52) U.S. Cl.
CPC ............ *C12M 41/44* (2013.01); *C12M 21/02* (2013.01); *C12M 41/06* (2013.01); *C12N 1/12* (2013.01); *C12Q 3/00* (2013.01)

(58) Field of Classification Search
CPC ....... C12M 21/02; C12M 41/06; C12M 41/10
See application file for complete search history.

(56) References Cited

U.S. PATENT DOCUMENTS 3,955,317 A    5/1976    Gudin
7,980,024 B2    7/2011    Berzin et al.
(Continued)

FOREIGN PATENT DOCUMENTS

JP    50-105881 A    8/1975
JP    1-153080 A    6/1989
(Continued)

OTHER PUBLICATIONS

International Search Report dated May 21, 2013 (Two (2) pages).

*Primary Examiner* — Nathan A Bowers
(74) *Attorney, Agent, or Firm* — Crowell & Moring LLP

(57) ABSTRACT

A system for culturing a photosynthetic organism such as a microalga has a liquid storage vessel for storing a liquid that absorbs more light in a short-wavelength range than light in a long-wavelength range, a culture vessel for storing a culture solution containing a photosynthetic organism to be cultured and disposed in the liquid storage vessel, a light quantity measuring unit for measuring the quantity of light that the culture vessel receives and a liquid depth controlling unit for controlling the liquid depth from the surface of the light-absorbing solution to the culture vessel based on the measurement result of the light quantity measuring unit. The light quantity measuring unit measures quantities of light which the culture vessel receives separately for different wavelength ranges. As a result, during the cultivation of a photosynthetic organism for the purpose of producing a biofuel or a useful substance, the increase in temperature and the defect caused by light under a strong light condition can be avoided and the decrease in photosynthetic efficiency can be made smaller.

12 Claims, 11 Drawing Sheets

(51) Int. Cl.
*C12M 1/34* (2006.01)
*C12N 1/12* (2006.01)
*C12Q 3/00* (2006.01)

(56) References Cited

U.S. PATENT DOCUMENTS

| | | | |
|---|---|---|---|
| 2008/0160591 A1 | 7/2008 | Willson et al. | |
| 2010/0105129 A1* | 4/2010 | Sanchez-Pina | C12M 21/02 435/286.5 |
| 2010/0287829 A1* | 11/2010 | Bussell | A01G 33/00 47/1.4 |
| 2011/0124087 A1* | 5/2011 | Meiser | C12M 21/02 435/243 |
| 2011/0281340 A1* | 11/2011 | Turner | C12M 21/02 435/257.1 |
| 2012/0164712 A1* | 6/2012 | Ellem | A01G 33/00 435/257.1 |
| 2012/0173023 A1* | 7/2012 | Fuxman | C12M 41/48 700/267 |
| 2013/0052719 A1* | 2/2013 | Lee | C12M 21/02 435/257.1 |
| 2013/0276365 A1* | 10/2013 | Franklin | C12M 21/02 47/1.4 |
| 2013/0326941 A1* | 12/2013 | Pickett | A01G 7/045 47/1.4 |
| 2013/0342844 A1* | 12/2013 | Tixier | C12N 1/14 356/409 |

FOREIGN PATENT DOCUMENTS

| | | |
|---|---|---|
| JP | 5-21698 U | 3/1993 |
| JP | 2010-514446 A | 5/2010 |
| WO | WO 2008/153202 A1 | 12/2008 |

* cited by examiner

[FIG. 1]
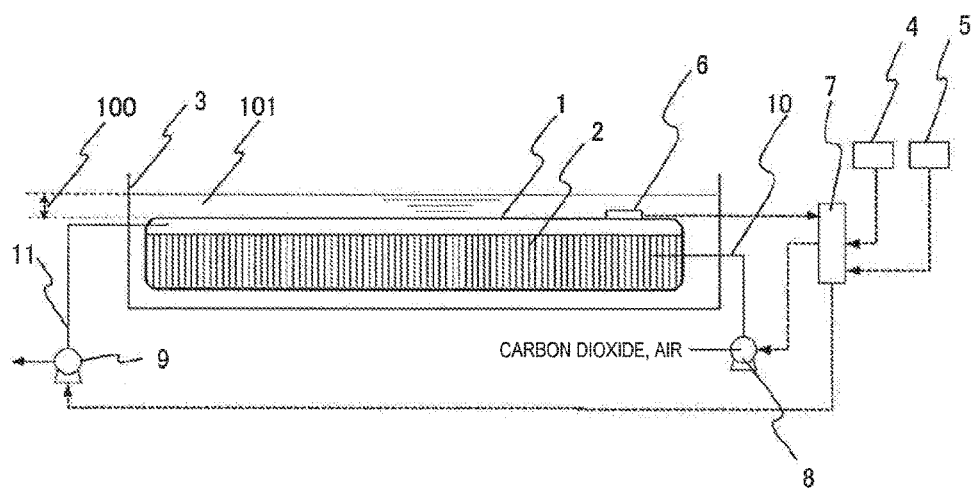

[FIG. 2]
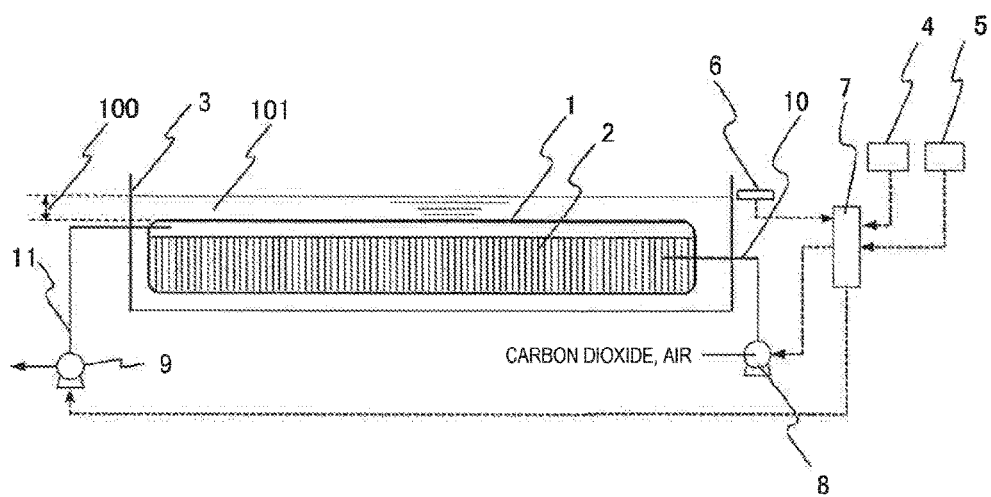

[FIG. 3]
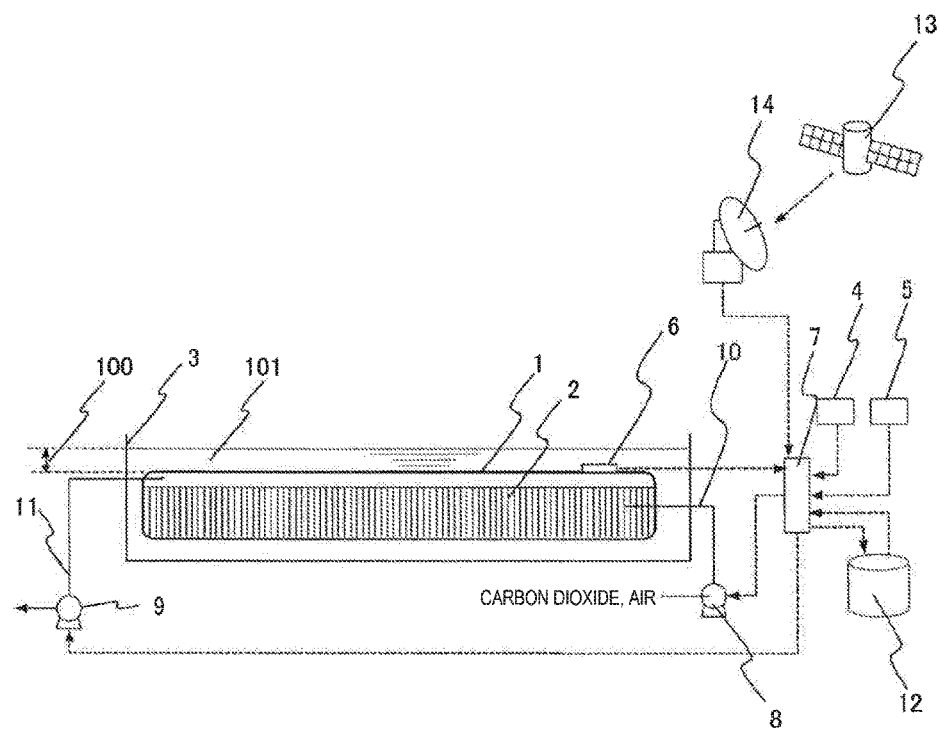

[FIG. 4]
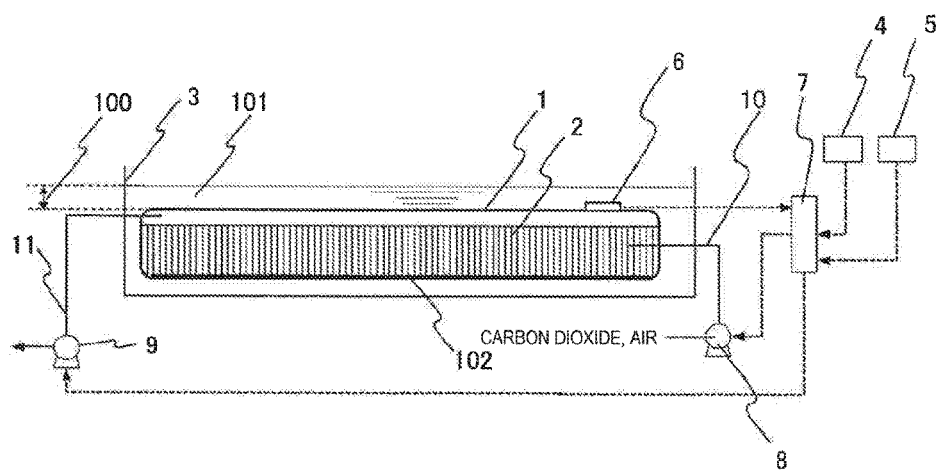

[FIG. 5]
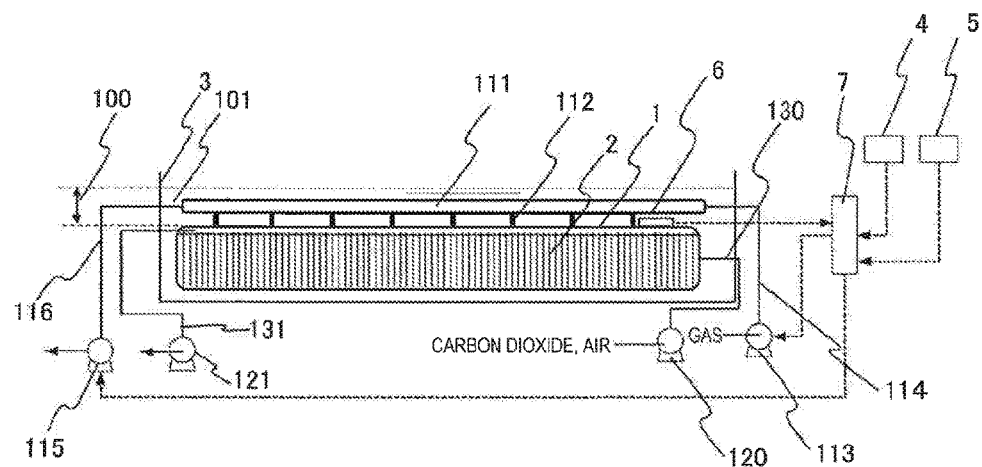

[FIG. 6]
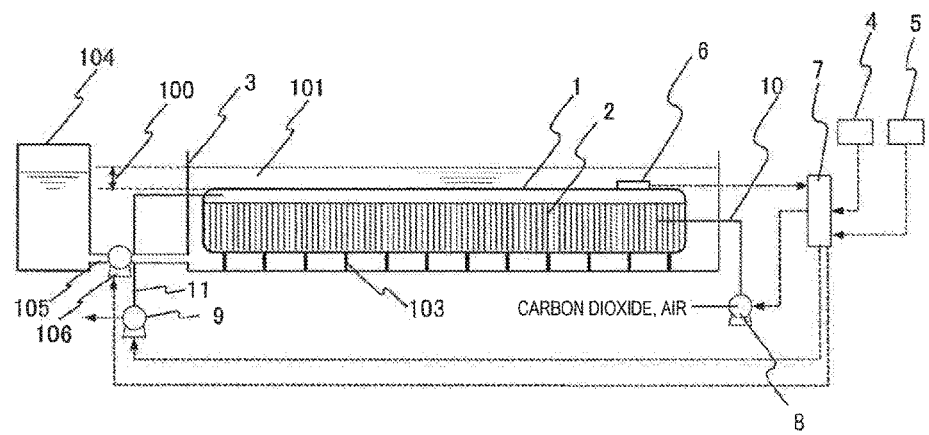

[FIG. 7]
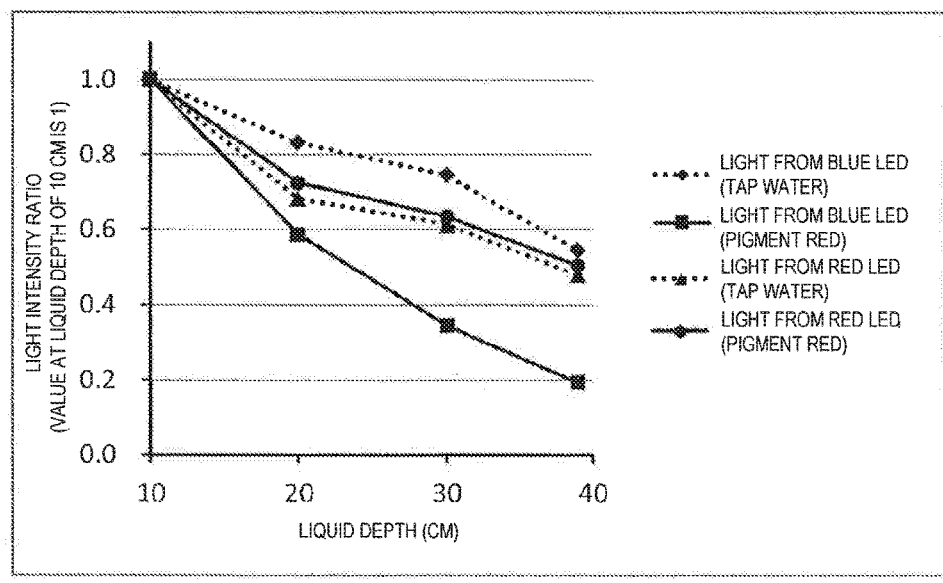

[FIG. 8]
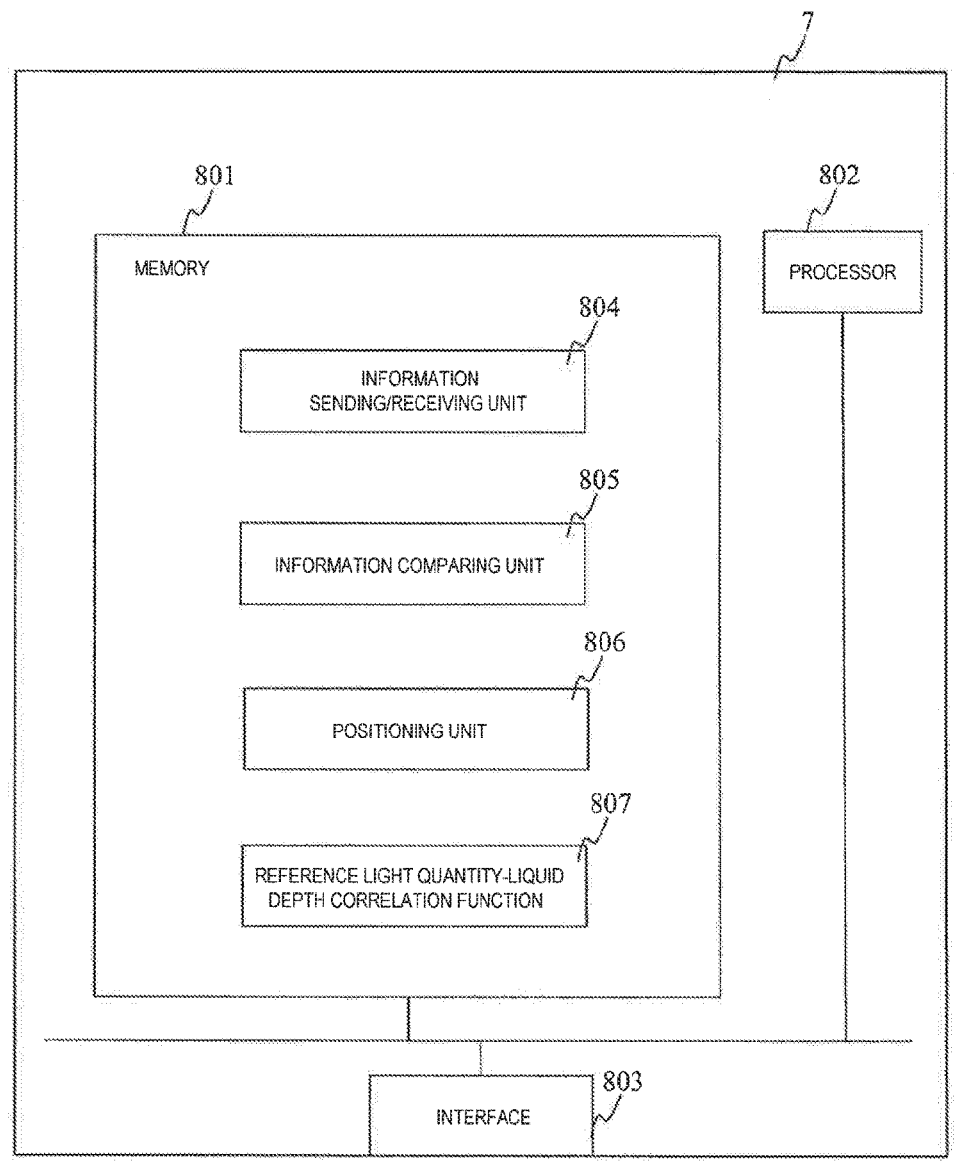

[FIG. 9]
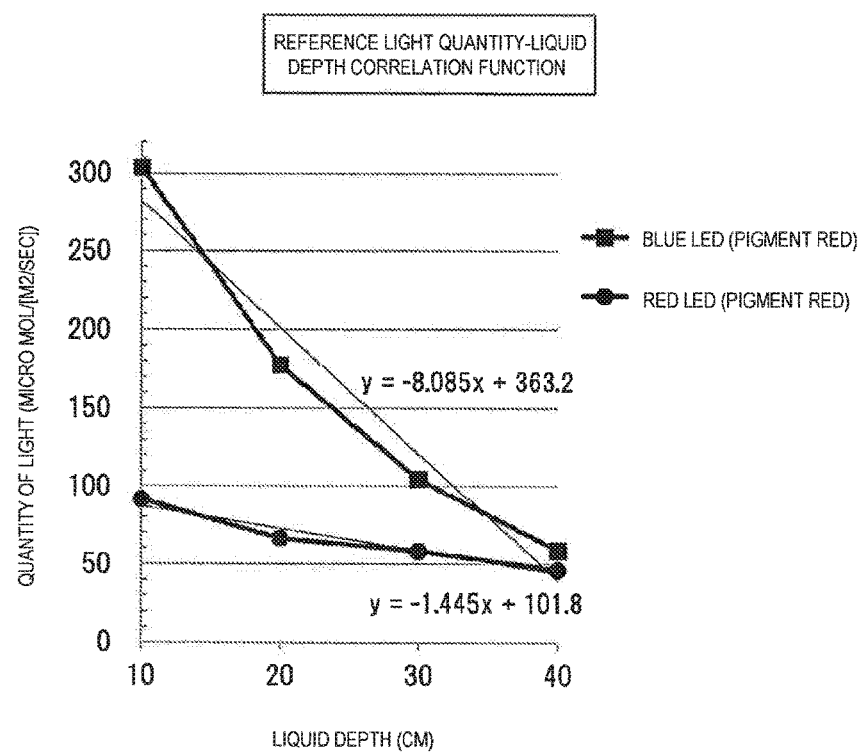

[FIG. 10]
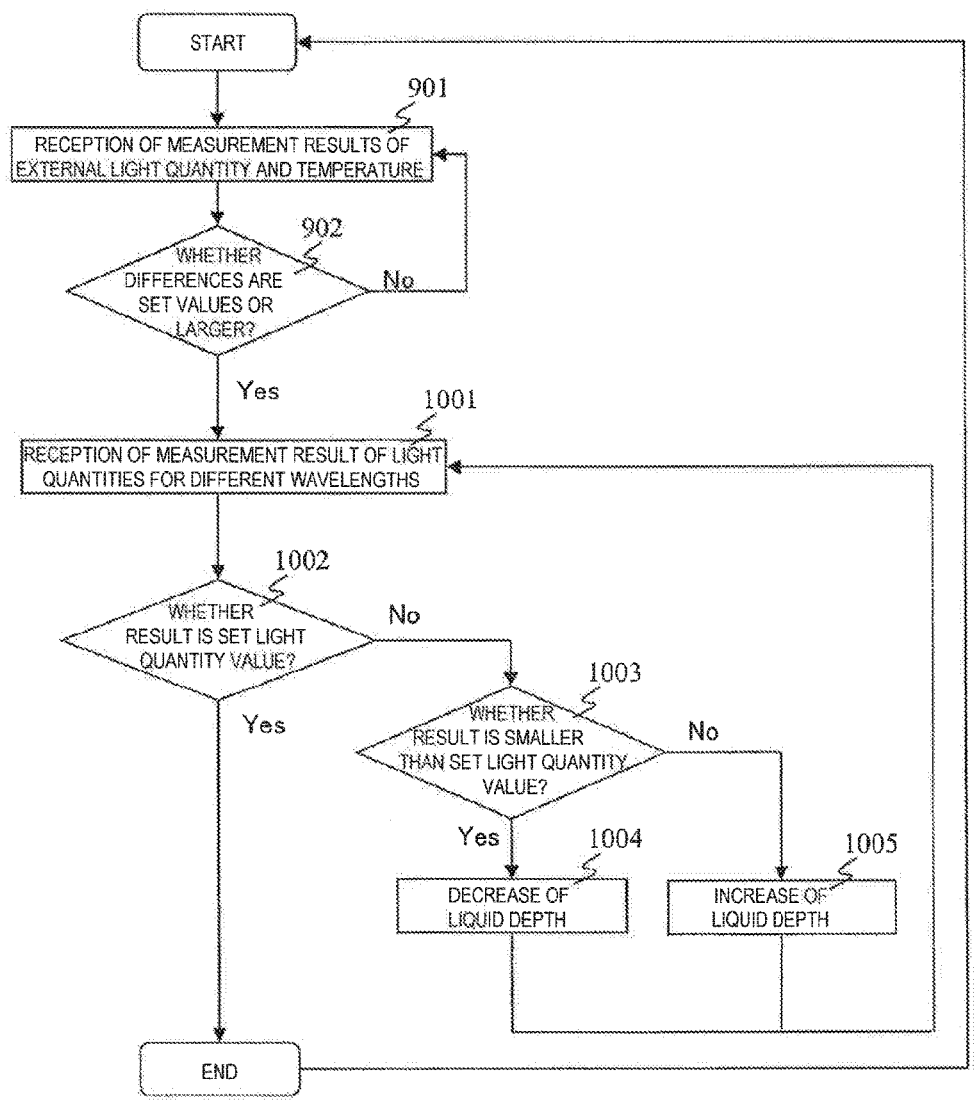

[FIG. 11]
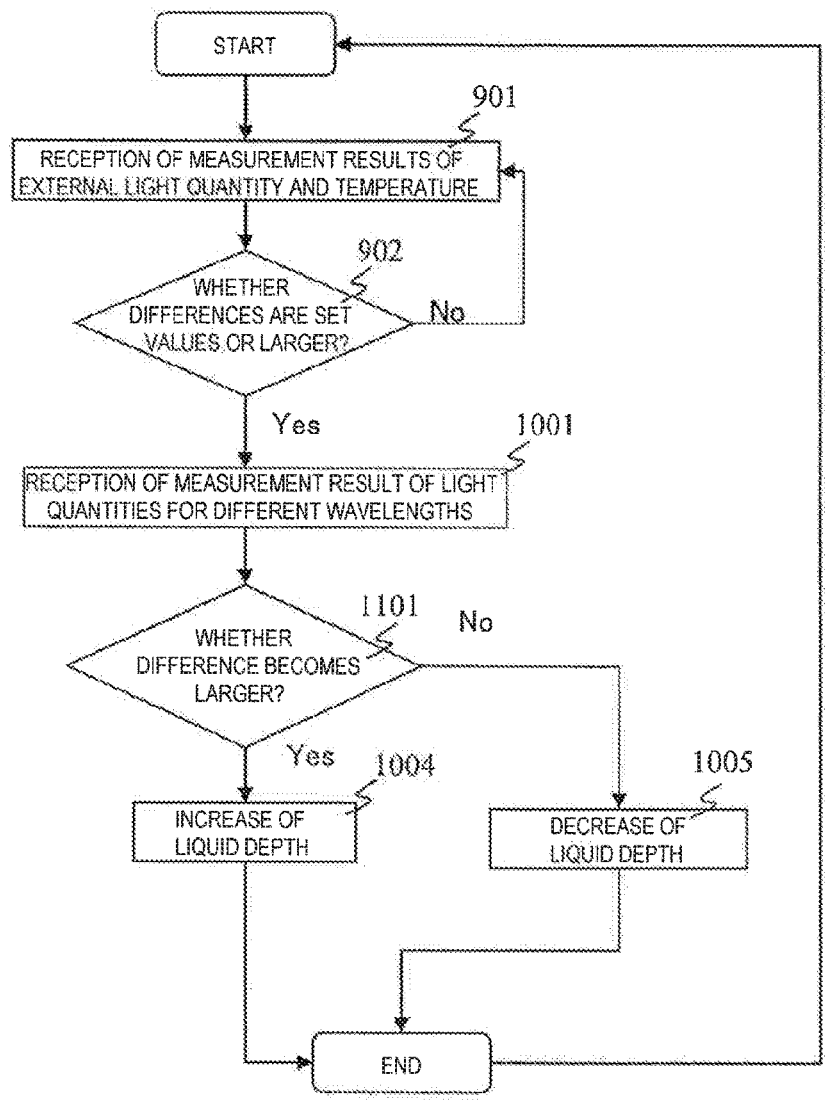

ORGANISM CULTURING SYSTEM AND ORGANISM CULTURING METHOD

TECHNICAL FIELD

The present invention relates to a system for culturing an organism and a method for culturing an organism. In particular, the invention relates to a technique for culturing a photosynthetic organism.

BACKGROUND ART

In recent years, microalgae which can produce biofuels through photosynthesis using sunlight and carbon dioxide in the atmosphere without competing against the food production have received attention. Currently, large-scale cultivation of algae for the purpose of producing biofuels and useful substances is often carried out outside in the tropics and subtropics where the amount of solar radiation is high so that the photosynthesis can be conducted to the maximum. However, the amount of solar radiation is excessive during the day in such regions, and the strong light raises the temperature of the culture environment. As a result, the growth and metabolism of microalgae are adversely affected, and thus it cannot be considered that the cultivation of microalgae in the regions is conducted under an optimum condition.

A technique which solves the above problem is described in U.S. Pat. No. 7,980,024 (PTL 1). This publication describes that "by floating a photobioreactor for cultivation on a pond or lake, heat is transferred between the water outside the photobioreactor and the liquid medium in the reactor". As a result, it becomes possible to prevent the temperature of the liquid medium in the photobioreactor for cultivation from rising high. Moreover, WO2008/153202 (PTL 2) describes "a reactor for photosynthesis which floats on the surface of water and which is made from a transparent, flexible material".

CITATION LIST

Patent Literature

PTL 1: U.S. Pat. No. 7,980,024
PTL 2 WO2008/153202

SUMMARY OF INVENTION

Technical Problem

PTL 1 merely describes that the culture vessel is just floating, and PTL 2 describes that the reactor floats on the surface of water. In these cases, the increase in the temperature of the liquid medium can be prevented by transferring heat with the water existing outside the reactor. However, since the intensity of solar irradiation itself is not reduced, the photosynthetic function deteriorates due to the defect caused by strong light.

That is, since the float photobioreactors of the conventional technology are placed on the surface of water, the amount of solar irradiation cannot be reduced, and it is difficult to avoid the defect caused by light under a strong light condition. On the other hand, if a photobioreactor can be sunk completely in the water of the external environment, rather than placing it on the surface of water, water absorbs the sunlight from the water surface. As a result, the sunlight reaching the reactor will be reduced and the amount of irradiation will decrease, and thus the defect caused by light under a strong light condition can be avoided.

In general, it is known that when water absorbs light, the amount of absorption varies with the wavelength of the light: the absorption by water becomes larger as the wavelength of the light is longer. With respect to light in the visible light range (400 to 700 nm), red light in a long-wavelength range (600 to 700 nm) is absorbed more by water and becomes weaker as compared to blue light in a short-wavelength range (400 to 500 nm). Here, it is known that blue light (400 to 500 nm) and red light (600 to 700 nm), which are in the visible light range, are both in the effective wavelength range of the photosynthesis of plants and microalgae. Therefore, when a photobioreactor is sunk completely in water, as described above, red light, which is in the effective wavelength range, becomes weak and consequently, the photosynthetic efficiency decreases, although the defect caused by light under a strong light condition can be avoided.

Therefore, the invention aims to provide an organism culture system including a function of controlling the light environment condition during the cultivation of photosynthetic organisms such as microalgae, in such a manner that the amount of solar irradiation is reduced but the components in the effective wavelength range of photosynthesis are reduced as little as possible, in order to avoid the increase in temperature and the defect caused by light under a strong light condition and to make the decrease in the photosynthetic efficiency small.

Solution to Problem

In an embodiment of the invention for solving at least one of the above problems, the organism culture system has: a liquid storage vessel for storing a light-absorbing solution that absorbs more light in a second wavelength range than light in a first wavelength range, wherein the second wavelength range is at a shorter wavelength side than the first wavelength range; a culture vessel for storing a culture solution containing a photosynthetic organism to be cultured and disposed in the liquid storage vessel; a light quantity measuring unit for measuring the quantity of light that the culture vessel receives; and a liquid depth controlling unit for controlling the liquid depth from the surface of the light-absorbing solution to the culture vessel based on the measurement result of the light quantity measuring unit.

In another embodiment of the invention for solving at least one of the above problems: a light-absorbing solution that absorbs more light in a second wavelength range than light in a first wavelength range is stored in a liquid storage vessel, wherein the second wavelength range is at a shorter wavelength side than the first wavelength range; a culture solution containing a photosynthetic organism to be cultured is stored in a culture vessel; the culture vessel is disposed in the liquid storage vessel; and the liquid depth from the surface of the light-absorbing solution to the culture vessel in the liquid storage vessel is controlled based on the quantity of light which the culture vessel receives.

Advantageous Effects of Invention

According to the invention, it becomes possible to avoid the increase in temperature and the defect caused by light under a strong light, condition during the cultivation of a photosynthetic organism and to make the decrease in the photosynthetic efficiency small. Problems, structures and effects other than those described above will be revealed in the explanation of Examples below.

BRIEF DESCRIPTION OF DRAWINGS

FIG. 1 An example of the diagram of the organism culture system according to Example 1 of the invention.

FIG. 2 An example of the diagram of the organism culture system according to Example 2 of the invention.

FIG. 3 An example of the diagram of the organism culture system according to Example 3 of the invention.

FIG. 4 An example of the diagram of the organism culture system according to Example 4 of the invention.

FIG. 5 An example of the diagram of the organism culture system according to Example 5 of the invention.

FIG. 6 An example of the diagram of the organism culture system according to Example 6 of the invention.

FIG. 7 A graph showing the relations between the absorption of red light and blue light and the liquid depth where pigment red 102 was used as an example of the substance capable of preferentially absorbing light in a specific wavelength range.

FIG. 7 An example showing the structure of the controller.

FIG. 9 A graph showing example reference light quantity-liquid depth correlation functions.

FIG. 10 An example showing the control flow in Example 1.

FIG. 11 An example showing the control flow in Example 2.

DESCRIPTION OF EMBODIMENTS

Examples of the invention are explained below using the figures. In this regard, it should be noted that the Examples are examples for carrying out the invention and do not limit the invention. Same reference numbers are given to same components in different figures.

Example 1

FIG. 1 is an example of the diagram showing the structure of the organism culture system of this Example.

The system has: a liquid storage was 3 which can store a liquid (light-absorbing solution) 101 in which a substance capable of preferentially absorbing light in a specific wavelength range is dissolved; a culture vessel 1 which is disposed in the vessel, can store a culture solution 2 containing a photosynthetic organism to be cultured such as a microalga and is transparent and a part or the whole of which is made from a flexible material (examples include polypropylene, polyethylene, ethylene vinyl acetate and polyvinyl chloride, though the flexible material is not particularly limited to the examples) and is deformable; a spectral light quantity measuring device 6 having functions capable of measuring quantities of light separately for desired wavelength ranges on the upper surface of the culture vessel 1 and sending the result to a controller 7; a pump 8 and an injection tube 10 for injecting carbon dioxide and air into the vessel; a pump 9 and a discharge tube 11 for discharging carbon dioxide and air from the vessel; an external light quantity measuring device 4 having functions capable of measuring the quantity of light in the environment around the culture vessel and sending the result to the controller 7; a temperature measuring device 5 having functions capable of measuring temperature and sending the result to the controller 7; and the controller 7 which receives the measured light quantity and temperature results sent from the light quantity and temperature measuring devices, determines the variable of the operation to inject or discharge carbon dioxide and air in the culture vessel and controls the operation.

The spectral light quantity measuring device 6 is an illuminometer or quantum sensor having a light receiving unit having an optical filter capable of transmitting light in a desired specific wavelength range, a multi-wavelength sensor capable of measuring for specific wavelength ranges, or the like. Carbon dioxide and air which are gases supplied to the pump 8 are supplied from a cylinder or another supply source, which are not shown in the figure.

Here, an example of the structure of the liquid 101 in this Example is explained using FIG. 7. FIG. 7 is a graph showing the relations between the absorption of red light and blue light and the liquid depth where pigment red 102, which is a substance that absorbs more light in the blue light range (400 to 500 nm) than light in the red light range (600 to 700 nm), was used as an example of the liquid 101 in which a substance capable of preferentially absorbing light in a specific wavelength range is dissolved. In general, red light is more likely to be absorbed by water, among light in the red light range (600 to 700 nm) and light in the blue light range (400 to 500 nm) which are effective for photosynthesis. Therefore, as the water depth increases, the proportion of the light component in the blue light range becomes higher and that in the red light range decreases, which is not a desirable light condition for photosynthesis. Accordingly, it is necessary to provide a method for reducing the light intensity to avoid the defect caused by light, while maintaining the proportions of components in the respective wavelength ranges to minimize the influence on the photosynthetic efficiency.

The liquid depths of an aqueous solution (concentration of 0.00006%) of pigment red 102, which is a substance that absorbs more light in the blue light range (400 to 500 nm) than light in the red light range (600 to 700 nm), and the amounts of absorption of red light and blue light were examined, and FIG. 7 shows the results. In the case of tap water, the decrease in the light intensity due to absorption of red light (light from a red LED: wavelength of 660 nm) was larger than that of blue light (light, from a blue LED: wavelength of 470 nm). On the other hand, in the case of the pigment red solution obtained by dissolving pigment red 102, which preferentially absorbs light in the blue light range (400 to 500 nm) the light intensity of blue light decreased more than that of red light, unlike the case of tap water. The results suggest that the light intensity can be decreased, while maintaining the proportions of components in the respective wavelength ranges, by suitably setting the liquid depth of the liquid in which a substance capable of preferentially absorbing light in a specific wavelength range is dissolved and the concentration of the dissolved substance.

Next, an example of the structure of the controller 7 is explained using FIG. 8. The controller 7 has a memory 801, a processor 802 and an interface 803. The memory 801 and the processor 802 are connected to an external device via the interface 803, and these devices can be controlled by sending and receiving a signal. A reference light quantity-liquid depth correlation function 807, which is explained below using FIG. 9, and respective programs for an information sending/receiving unit 80, an information comparing unit 805 and a positioning unit 806 are stored in the memory 801. In the controller 7, the processor 802 reads and executes the programs to conduct the processes related to the control of the liquid depth as described below.

The reference light quantity-liquid depth correlation function 807 is explained below using FIG. 9.

FIG. 9 is a graph showing the correlations between the depth of a liquid in which a substance that absorbs more light in the blue light range than light in the red light range is dissolved and the quantities of red light and blue light which decrease with the liquid depth, in the example case shown in FIG. 7 where light in the blue light range (400 to 500 nm) is specifically reduced without significantly reducing light in the red light range (600 to 700 nm). In FIG. 9, each of the light quantity-liquid depth correlations is approximated using a linear function but the approximate function varies with the wavelength range of the light to be controlled and with the properties of the substance used for absorbing light of a specific wavelength. An approximate expression that is considered to be the most suitable may be used for each case, and the approximation is not necessarily limited to approximation using a linear function.

From the slopes of the approximate expressions in FIG. 9, the decrease in the red light quantity per liquid depth of 1 cm is 1.445 $\mu mol/(m^2 \cdot sec)$ and the decrease in the blue light quantity per liquid depth of 1 cm is 8.085 $\mu mol/(m^2 \cdot sec)$, in the example shown in FIG. 7. In this manner, the coefficients of the decreases in the light quantities per unit liquid depth of the liquid in which a substance that absorbs light in a specific wavelength range is dissolved are experimentally obtained in advance for the light in a wavelength range which should be reduced by absorption and for the light in a wavelength range which is not affected by absorption or only slightly affected and which should be applied to the organism to be cultured, and the liquid depth at which the desirable intensity of light irradiation can be achieved is calculated using the coefficients. In the case shown in FIG. 9, when the light irradiation is controlled based on blue light to be reduced, the liquid depth value should be calculated and used for the control to satisfy the equation: desired intensity of blue light irradiation $[\mu mol/(m^2 \cdot sec)]$=(blue light quantity at liquid depth of 0 cm $[\mu mol/(m^2 \cdot sec)]$)– 8.085× liquid depth (cm).

In addition, when the intensity of light irradiation is set based on the intensity of red light irradiation, the liquid depth value should be calculated and used for the control to satisfy the equation: desired intensity of red light irradiation $[\mu mol/(m^2 \cdot sec)]$=(red light quantity at liquid depth of 0 cm $[\mu mol/(m^2 \cdot sec)]$)–1.445×liquid depth (cm).

The control of the liquid depth by the controller 7 is explained below using the flowchart shown in FIG. 10. First, the information sending/receiving unit 804 sends signals ordering measurement to the external light quantity measuring device 4 and the temperature measuring device 5 in the environment around the culture vessel to start the measurement in the external light quantity measuring device 4 and the temperature measuring device 5 and receives the respective measurement results (901). Here, the step 901 is repeated at least twice at a time interval which is set in advance. The information comparing unit 805 obtains the measurement results through the information sending/receiving unit 804 and calculates the differences of the repeatedly measured values. When the differences exceed values that are set in advance (902), the information comparing unit 805 determines that the external environment changes, in other words the solar irradiation condition changes, and sends to the information sending unit 804 a signal ordering to start the measurement in the spectral light quantity measuring device 6. When the order signal is sent, the sending/receiving unit 804 obtains the measurement result of the spectral light quantity measuring device 6. The measurement result of the spectral light quantity measuring device 6 compares with a light quantity value of the intensity of solar irradiation which is set in advance for the organism to be cultured, which calculated from the reference light quantity-liquid depth correlation function 807 (1002). When the measurement result of the spectral light quantity measuring device 6 is the set light quantity value, the procedure is ended, and the steps from the start are carried out.

On the other hand, when the measurement result of the spectral light quantity measuring device 6 is widely different from the set light quantity value, the information comparing unit 805 determines whether or not the measurement result of the spectral light quantity measuring device 6 is smaller than the set light quantity value (1003). When the measurement result of the spectral light quantity measuring device 6 is larger than the set light quantity value, as a result of the comparison by the information comparing unit 805, the positioning unit 806 operates the discharge pump 9 to discharge the gas in the culture vessel 1 (for example, carbon dioxide and/or air) through the discharge tube 11, thereby reducing the buoyancy of the culture vessel 1. As a result, the position of the culture vessel 1 in the liquid storage vessel 3 moves downward in the vertical direction, and a liquid depth 100 is thus increased (1005). On the other hand, when the measurement result of the spectral light quantity measuring device 6 is smaller than the set light quantity value, as a result of the comparison by the information comparing unit 805, the injection pump 8 is operated to inject a gas into the culture vessel 1 through the injection tube 10, thereby increasing the buoyancy of the culture vessel 1. As a result, the position of the culture vessel 1 in the liquid storage vessel 3 moves upward in the vertical direction, and the depth 100 thus decreases. In this manner, by operating the pump 8 or 9 by sending a control signal and changing the volume of the gas, such as carbon dioxide and/or air, in the culture vessel 1, the positioning unit 806 controls the buoyancy of the culture vessel 1 and moves the position of the culture vessel 1 in the liquid storage vessel 3 in the vertical direction.

After the positioning unit 806 has adjusted the liquid depth (the step 1004 and the step 1005), the step 1001 is carried out. Through the control of the information sending/receiving unit 804, the spectral light quantity measuring device 6 disposed on the surface of the culture vessel 1 conducts the measurement again, and the step 1002 and the subsequent steps are conducted by the information comparing unit 805 and the positioning unit 806.

In this manner, the controller 7 repeats the operation through the feedback control until the quantity of light measured by the spectral light quantity measuring device 6 disposed on the surface of the culture vessel 1 becomes the desired value. During the day, the values measured by the external light quantity measuring device which measures the quantity of light in the environment around the culture vessel, and by the temperature measuring device 5, which measures the temperature, change with time. Therefore, the positional control of the culture vessel 1 in the vertical direction is continued during the day so that the value of the spectral light quantity measuring device 6 disposed on the surface of the culture vessel becomes the desired value.

As described above, in this Example, an example organism culture system has been described, which can avoid the increase in temperature and the defect caused by light under a strong light condition during the cultivation of a photosynthetic organism and make the decrease in the photosynthetic efficiency small, by providing: the liquid storage vessel 3 for storing the liquid (light-absorbing solution) 101, which absorbs more light in a second wavelength range, such as the blue light range (400 to 500 nm), than light in a first wavelength range, such as the red light range (600 to 700 nm), wherein the second wavelength range is at a shorter wavelength side than the first wavelength range; the culture vessel 1 for storing the culture solution containing a photosynthetic organism to be cultured and disposed in the liquid storage vessel; a light quantity measuring unit, such as the spectral light quantity measuring device 6, for measuring the quantity of light that the culture vessel 1 receives; and a liquid depth controlling unit, such as the controller 7, for controlling the liquid depth from the surface of the liquid (light-absorbing solution) 101 to the culture vessel 1 based on the measurement result of the light quantity measuring unit.

Example 2

FIG. 2 is a diagram showing the structure of Example 2 for controlling the position of the culture vessel 1 in the vertical direction by the controller 7, which is different from that of Example 1. In this Example, the spectral light quantity measuring device 6 is provided apart from the culture vessel 1 and in a position corresponding to a set liquid depth in the depth direction of the liquid storage vessel 3, for example in a position corresponding to the liquid depth of 0 as shown in FIG. 2. In the example structure shown in FIG. 2, the spectral light quantity measuring device 6 is provided outside the liquid storage vessel 3 in a position corresponding to the liquid depth of 0. The liquid depth is controlled using the values measured by the external light quantity measuring device 4 for measuring the quantity of light in the environment around the culture vessel and the temperature measuring device 5 for measuring the temperature and using the value measured by the spectral light quantity measuring device 6 disposed in a position corresponding to the liquid depth of the liquid storage vessel 3 of 0. The control of the liquid depth by the controller 7 in this Example is explained below using the flowchart shown in FIG. 11.

First, the information sending/receiving unit 804 sends signals ordering measurement to the external light quantity measuring device 4 and the temperature measuring device 5 in the environment around the culture vessel to start the measurement in the external light quantity measuring device 4 and the temperature measuring device 5 and receives the respective measurement results (901). Here, the step 901 is repeated at least twice at a time interval which is set in advance. The information comparing unit 805 obtains the measurement results through the information sending/receiving unit 804 and calculates the differences of the repeatedly measured values. When the differences exceed values that are set in advance (902), the information comparing unit 805 determines that the external environment changes, in other words the solar irradiation condition changes, and sends to the information sending unit 804 a signal ordering to start the measurement in the spectral light quantity measuring device 6. When the order signal is sent, the information comparing unit 805 obtains the measurement result of the spectral light quantity measuring device 6 which the information sending/receiving unit 804 has received (1001).

Next, the acquisition of the measurement result of the spectral light quantity measuring device 6 is repeated at least twice at a time interval which is set in advance, and the differences of the measurement values are calculated. The liquid depth is controlled according to the differences: the liquid depth is increased when the difference becomes larger with the time, while the liquid depth is reduced when the difference becomes smaller (1101). The degree or the liquid depth control here is determined based on the reference light quantity-liquid depth correlation function 807, and the liquid depth 100 is adjusted through the adjustment of the buoyancy of the culture vessel 1 by operating the discharge pump 9 with the positioning unit 806 and discharging the gas in the culture vessel 1 (for example, carbon dioxide and/or air) through the discharge tube 11, or by injecting a gas through the injection tube 10 (1004 and 1005).

In this manner, by operating the pumps 8 and 9 by sending a control signal and changing the volume of the gas, such as carbon dioxide and/or air, in the culture vessel 1, the positioning unit 806 controls the buoyancy of the culture vessel 1 and moves the position of the culture vessel 1 in the liquid storage vessel 3 in the vertical direction. After the positioning unit 806 has adjusted the liquid depth (1004 and 1005), the operation is ended for a while. Then, after a set period of time, the start step is carried out to continue the control of the liquid depth.

In the embodiment described in Example 2, the liquid depths of two or more liquid storage vessels can be controlled based on the information of one spectral light quantity measuring device 6.

Example 3

FIG. 3 is a diagram showing another Example, namely Example 3, for controlling the position of the culture vessel in the vertical direction by the controller 7. This Example shows an embodiment in which meteorological information, such as occurrence and movement of clouds, which affects the amount of solar radiation in the area where the organism culture system has been installed and which is obtained from a weather satellite 13 via an information receiving facility 14 is related to the controller 7. The information obtained from the weather satellite 13 covers a wide region including the area where the organism culture system has been installed, and it is necessary to forecast the change in the amount of solar radiation or the like in the area where the organism culture system has been installed from the obtained condition of clouds (the cloud's area, the thickness in the vertical direction, the speed and the like). Accordingly, it is necessary to establish and provide a database 12 of the meteorological information in the area in advance. By relating the information obtained from the weather satellite 13 to the database 12, the change in the amount of solar radiation in the area is forecasted. By starting the operation shown in FIG. 10 or 11 based on the forecast. The control can be started before the actual change in the amount of solar radiation, and as a result, more accurate control of the position of the culture vessel 1 in the vertical direction becomes possible.

Example 4

FIG. 4 is a diagram showing another embodiment of the culture vessel 1 which can store the culture solution 2 containing the organism to be cultured and is transparent and a part or the whole of which is made from a flexible material and is deformable. An undeformable, strong material 102 is disposed at the bottom of the culture vessel 1 in the horizontal direction. The undeformable, strong material is a synthetic resin such as plastic, carbon fiber-reinforced plastic reinforced with carbon fibers, a metal or the like, but the undeformable, strong material is not necessarily limited to these materials. Even when the deformable part of the culture vessel 1 deforms into an uneven form, the position of the culture vessel 1 in the liquid storage vessel 3 in the horizontal direction can be maintained by providing the undeformable material 102. As a result, the liquid depth over the upper surface of the culture vessel 1 can be kept constant.

Example 5

FIG. 5 is a diagram showing the structure of Example 5 relating to an organism culture system in which the position of the culture vessel 1 in the vertical direction can be controlled by providing a buoyant body 111 which is connected to the culture vessel 1 and causes buoyancy, unlike Examples 1 to 4 in which the liquid depth is controlled by adjusting the buoyancy of the culture vessel 1.

The components with the same reference signs as those shown in FIG. 1 which have been explained above, the parts having the same functions, the flow of the buoyancy control and the like are not explained here. FIG. 5 shows a structure containing a deformable buoyant body 111 which is connected to the culture vessel 1, made from a flexible material and can store a gas, a connector 112 for connecting to the culture vessel 1, a pump 113 and an injection tube 114 for injecting a gas into the buoyant body and a discharge pump 115 and a discharge tube 116 for discharging the gas, and a structure containing a pump 120 and an injection tube 130 for supplying carbon dioxide or air necessary for the growth of the organism to be cultured to the culture solution 2 containing the organism to be cultured in the culture vessel 1 and a pump 121 and a discharge tube 131 for discharging. The method for controlling the liquid depth in this Example is explained.

Based on the measurement results of the external light quantity measuring device 4 and the temperature measuring device 5 in the environment around the culture vessel and of the spectral light quantity measuring device 6 for measuring the quantities of light separately for different wavelength ranges on the surface of the culture vessel, when the intensity of solar irradiation is widely different from a value which is set in advance for the organism to be cultured, the pump 120 or 121 is operated by a signal from the controller 7 to change the volume of the gas in the buoyant body 111 and to control the buoyancy of the buoyant body 111, and the position of the culture vessel 1 connected to the buoyant body 111 in the liquid storage vessel 3 is moved in the vertical direction. After the operation, the spectral light quantity measuring device 6 disposed on the surface of the culture vessel conducts the measurement again. When the measured quantity of light is excessive as compared to the desired quantity of light, the controller 7 operates the discharge pump 121 to discharge the gas in the buoyant body 111 through the discharge tube 131, thereby reducing the buoyancy of the buoyant body 111. As a result, the position of the culture vessel 1 in the liquid storage vessel 3 moves downward in the vertical direction, and the liquid depth 100 thus increases.

On the other hand, when the measured quantity of light is smaller than the desired quantity of light, the injection pump 120 is operated to inject a gas into the buoyant body 111 through the injection tube 130, thereby increasing the buoyancy of the buoyant body 111. As a result, the position of the culture vessel 1 connected to the buoyant body 111 in the liquid storage vessel 3 moves upward in the vertical direction, and the liquid depth 100 thus decreases. The operation through the feedback control is repeated until the quantity of light measured by the spectral light quantity measuring device 6 disposed on the surface of the culture vessel becomes the desired value. The flows for controlling the buoyancy explained in Examples 1 to 4 can be applied except for the processes of increasing/decreasing the liquid depth.

During the day, the values measured by the external light quantity measuring device 4, which measures the quantity of light in the environment around the culture vessel, and by the temperature measuring device 5, which measures the temperature, change with time. Therefore, the positional control of the culture vessel 1 in the vertical direction by the buoyant body 111 is continued during the day so that the value of the spectral light quantity measuring device 6 disposed on the surface of the culture vessel becomes the desired value. According to Example 5, the kind of gas injected into the buoyant body is not particularly limited and any gas component can be used, while the gas used for the liquid depth control in Examples 1 to 4 is limited to a gas which does not affect the growth of the organism to be cultured in the culture vessel (carbon dioxide and air).

Example 6

FIG. 6 is an example of the diagram showing the structure of the organism culture system according to Example 6 in which the liquid depth 100 can be controlled by changing the amount of the liquid 101 in which a substance capable of preferentially absorbing light in a specific wavelength range is dissolved in the liquid storage vessel 3, rather than controlling the liquid depth by adjusting the buoyancy of the culture vessel 1.

In FIG. 6, the culture vessel 1 is fixed in the liquid storage vessel 3 with a connector 103. The liquid storage vessel 3 is connected to a storage tank 104 containing the liquid 101 in which the substance capable of preferentially absorbing light in a specific wavelength range is dissolved via a connection pipe 105, and the amount of the liquid 101 in the liquid storage vessel 3 can be changed using an injection/discharge pump 106 provided in the connection pipe.

The method for controlling the liquid depth in this Example is explained below. Based on the measurement results of the external light quantity measuring device 4 and the temperature measuring device 5 in the environment around the culture vessel and of the spectral light quantity measuring device 6 for measuring the quantities of light separately for different wavelength ranges on the surface of the culture vessel, when the intensity of solar irradiation is widely different from a value which is set in advance for the organism to be cultured, the injection/discharge pump 106 is operated by a signal from the controller 7 to inject the liquid 101 into the liquid storage vessel 3 or discharge the liquid 101 from the liquid storage vessel 3 through the connection pipe 105. The water level of the liquid 101 in the liquid storage vessel 3 is thus controlled.

Here, when the culture vessel 1 contains a certain volume of a gas component and is fixed with the connector 103, the water level of the liquid 101 will be above the upper surface of the culture vessel 1 and there will be a layer of the liquid 101 over the culture vessel 1, which results in the liquid depth 100. The liquid depth 100 changes with the change of the water level of the liquid 101 in the liquid storage vessel 3, and the liquid depth 100 can be thus controlled. In practice, the spectral light quantity measuring device 6 disposed on the surface of the culture vessel conducts the measurement, and when the measured quantity of light is excessive as compared to the desired quantity of light, the controller 7 operates the injection/discharge pump 106 to inject the liquid 101 from the storage tank 104 into the liquid storage vessel 3 through the connection pipe 105. As a result, the water level of the liquid 101 in the liquid storage vessel 3 rises, and the liquid depth 100 thus increases.

On the other hand, when the measured quantity of light is smaller than the desired quantity of light, the injection/discharge pump 106 is operated to discharge the liquid 101 from the liquid storage vessel 3 into the storage tank 104 through the connection pipe 105. As a result, the water level of the liquid 101 in the liquid storage vessel 3 lowers, and the liquid depth 100 thus decreases. The flows for controlling the buoyancy explained in Examples 1 to 4 can be applied except for the processes of increasing/decreasing the liquid depth.

The operation through the feedback control is repeated until the quantity of light measured by the spectral light quantity measuring device 6 disposed on the surface of the culture vessel becomes the desired value. During the day, the values measured by the external light quantity measuring device 4, which measures the quantity of light in the environment around the culture vessel, and by the temperature measuring device 5, which measures the temperature, change with time. Therefor, the control of the liquid depth 100 is continued during the day so that the value of the spectral light quantity measuring device 6 disposed on the surface of the culture vessel becomes the desired value.

According to this Example, the positional control of the culture vessel 1 in the horizontal direction in the liquid in the liquid storage vessel 3 becomes easy when a deformable culture vessel 1 is used, as compared to other Examples.

The invention made by the present inventors has been explained above referring to specific examples based on the embodiments, but it is needless to mention, that the invention is not limited to the embodiments and various modifications are possible as long as they do not go beyond its gist.

REFERENCE SIGNS LIST

1: culture vessel, 2: culture solution containing organism to be cultured, 3: liquid storage vessel, 4: light quantity measuring device, 5: temperature measuring device, 6: spectral light quantity measuring device, 7: controller, 8, 9: pump, 10: injection tube, 11: discharge tube, 12: database, 13: weather satellite, 14: information receiving facility, 100: liquid depth, 101: liquid in which substance capable of preferentially absorbing light in specific wavelength range is dissolved, 102: undeformable, strong material, 103, 112: connector, 104: storage tank, 105: connection pipe, 106: injection/discharge pump, 111: buoyant body, 113: injection pump, 114: injection tube, 115: discharge pump, 116: discharge tube, 120, 121: pump, 130: injection tube, 131: discharge tube, 801: memory, 802: processor, 803: interface, 804: information sending/receiving unit, 805: information comparing unit, 806: positioning unit and 807: reference light quantity-liquid depth correlation function.

The invention claimed is:

1. An organism culture system comprising:
   a liquid storage vessel for storing a light-absorbing solution that absorbs more light in a second wavelength range than light in a first wavelength range, wherein the second wavelength range is at a shorter wavelength side than the first wavelength range,
   a culture vessel for storing a culture solution containing a photosynthetic organism to be cultured and disposed in the liquid storage vessel,
   a first light quantity measuring unit for measuring the quantity of light that the culture vessel receives separately for different wavelength ranges,
   a second light quantity measuring unit for measuring the quantity of external light surrounding the liquid storage vessel, and
   a liquid depth controlling unit for controlling the liquid depth from the surface of the light-absorbing solution to the culture vessel in the liquid storage vessel based on the measurement result of the first light quantity measuring unit,
   wherein light intensity is decreased, while the proportion of light in the first wavelength range and the second wavelength range is maintained, by controlling the liquid depth.

2. The organism culture system according to claim 1, wherein the liquid depth controlling unit controls the liquid depth by controlling the buoyancy exerted on the culture vessel in the light-absorbing solution.

3. The organism culture system according to claim 2, wherein the liquid depth controlling unit controls the buoyancy by controlling the volume of a gas in the culture vessel.

4. The organism culture system according to claim 3, wherein the gas in the culture vessel controlled by the liquid depth controlling unit contains carbon dioxide.

5. The organism culture system according to claim 2, wherein
   the culture vessel has a buoyant body capable of storing a gas, and
   the liquid depth controlling unit controls the buoyancy by controlling the volume of the gas in the buoyant body.

6. The organism culture system according to claim 1, wherein
   the culture vessel is fixed in a set position in the liquid storage vessel, and
   the liquid depth controlling unit controls the liquid depth by adjusting the amount of the light-absorbing solution in the liquid storage vessel.

7. The organism culture system according to claim 1, wherein the liquid depth controlling unit determines whether or not to control the liquid depth based on the quantity of external light.

8. The organism culture system according to claim 1, further comprising an external temperature measuring unit for measuring the external temperature of the liquid storage vessel,
   wherein the liquid depth controlling unit determines whether or not to control the liquid depth based on the external temperature.

9. The organism culture system according to claim 1, wherein the light-absorbing solution stored in the liquid storage vessel is a liquid in which a pigment that absorbs more light in the second wavelength range than light in the first wavelength range is dissolved.

10. The organism culture system according to claim 1, wherein the liquid depth controlling unit stores correlations between the liquid depth and the quantities of light in the first and second wavelength ranges in advance and controls the liquid depth based on the correlations.

11. The organism culture system according to claim 1, further comprising a receiving unit for receiving information from an artificial satellite,
    wherein the liquid depth controlling unit controls the liquid depth based on information on the weather which the receiving unit receives from the artificial satellite.

12. A method for culturing an organism, comprising:
- storing a light-absorbing solution that absorbs more light in a second wavelength range than light in a first wavelength range in a liquid storage vessel, wherein the second wavelength range is at a shorter wavelength side than the first wavelength range,
- storing a culture solution containing a photosynthetic organism to be cultured in a culture vessel,
- disposing the culture vessel in the liquid storage vessel,
- measuring the quantity of light that the culture vessel receives separately for different wavelength ranges using a first measuring unit,
- measuring the quantity of external light surrounding the liquid storage vessel using a second light quantity measuring unit, and
- controlling the liquid depth from the surface of the light-absorbing solution to the culture vessel in the liquid storage vessel based on the quantity of external light surrounding the liquid storage vessel and on the quantity of light measured for different wavelength ranges on the surface of the culture vessel,
- wherein light intensity is decreased while the proportion of light in the first wavelength range and the second wavelength range is maintained, by controlling the liquid depth.

* * * * *